United States Patent [19]

Bajnógel et al.

[11] Patent Number: 5,486,528
[45] Date of Patent: Jan. 23, 1996

[54] BASIC ETHERS AND PROCESS FOR THE PREPARATION THEREOF

[75] Inventors: Judit Bajnógel; Gábor Blaskó; Zoltán Budai; Éva Schmidt; András Egyed; Márton Fekete; István Gacsályi; István Gyertyán; Tibor Mezei; Kalára Reiter née Esses; Gyula Simig; Katalin Szemerédi; Enikő Szirt née Kiszelly, all of Budapest, Hungary

[73] Assignee: Egis Gyogyszergyar Rt., Budapest, Hungary

[21] Appl. No.: 226,089

[22] Filed: Apr. 11, 1994

[30] Foreign Application Priority Data

Apr. 9, 1993 [HU] Hungary ................. 93 01040

[51] Int. Cl.$^6$ ............... A61K 31/15; C07C 251/48
[52] U.S. Cl. ............ 514/331; 514/238.2; 514/255; 514/318; 514/422; 514/428; 514/640; 544/124; 544/146; 544/162; 544/364; 544/398; 546/192; 546/193; 546/212; 546/214; 546/232; 546/338; 548/566; 548/569; 562/517; 562/595; 564/114; 564/256
[58] Field of Search ............... 546/192, 193, 546/338, 212, 214, 232; 548/569, 566; 544/124, 146, 364, 162, 398; 562/597, 595; 564/114, 256; 514/238.2, 255, 318, 331, 422, 428, 640

[56] References Cited

U.S. PATENT DOCUMENTS 5,166,416  11/1992  Congy ........................ 562/114
5,378,716   1/1995  Hamanaka .................... 514/333

FOREIGN PATENT DOCUMENTS 82059  6/1983  European Pat. Off. .

OTHER PUBLICATIONS

Uuterhalt et al "Kurzmitteilungen. Ungesattigtte Oxime" Arch Pharm. 316 469–471 (1983).

Congy et al "Biochemical & Pharmacological Properties of SR 46349B" J. Pha. Exp. Ther. 262 759–768 (1992).

*Primary Examiner*—Ceila Chang
*Attorney, Agent, or Firm*—Beveridge, DeGrandi, Weilacher & Young

[57] ABSTRACT

Novel basic ether of general formula (I),

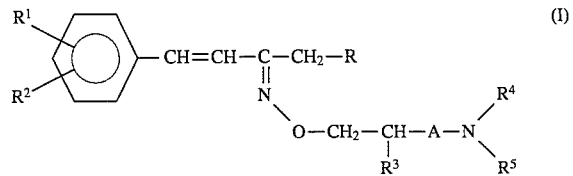

wherein $R^1$ and $R^2$ are independently hydrogen, halogen or $C_{1-4}$ alkoxy, or together they represent a 3,4-methylenedioxy group, R stands for $C_{1-8}$ alkyl, $R^3$ represents hydrogen, $C_{1-4}$ alkyl or hydroxy, A is a valency bond or methylene group, $R^4$ and $R^5$ are independently hydrogen, $C_{1-12}$ alkyl or $C_{1-12}$ alkenyl, or $R^4$ and $R^5$ form together with the adjacent nitrogen atom 1-pyrrolidinyl, 1-piperidinyl, morpholino or 1-piperazinyl groups, stereo and optically active isomers and their possible mixtures, acid-addition salts and quaternary ammonium derivatives thereof. The basic ethers have antiulceric and anxiolytic activities.

8 Claims, No Drawings

BASIC ETHERS AND PROCESS FOR THE PREPARATION THEREOF

The present invention relates to novel, pharmaceutically active basic ethers, a process for the preparation thereof, pharmaceutical compositions comprising the same, to the use of the said basic ethers for the treatment of diseases and for the preparation of pharmaceutical compositions suitable for the treatment of diseases.

According to an aspect of the present invention there are provided new basic ethers of general formula (I), wherein

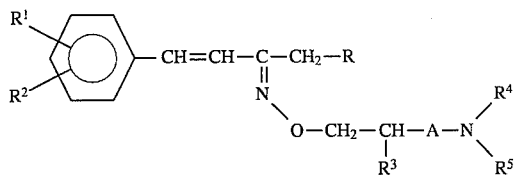

$R^1$ and $R^2$ are independently hydrogen, halogen or $C_{1-4}$ alkoxy, or together they represent a 3,4-methylenedioxy group, R stands for $C_{1-8}$ alkyl, $R^3$ represents hydrogen, $C_{1-4}$ alkyl or hydroxy, A is a valency bond or a methylene group, $R^4$ and $R^5$ are independently hydrogen, $C_{1-12}$ alkyl or $C_{1-12}$ alkenyl, or $R^4$ and $R^5$ form together with the adjacent nitrogen atom a 4- to 7-membered ring optionally comprising an oxygen, sulfur or a further nitrogen atom, which latter may carry a phenyl, benzyl or $C_{1-4}$ alkyl substituent, stereo and optically active isomers and their possible mixtures, acid addition salts and quaternary ammonium derivates thereof.

The compounds according to the present invention possess valuable antiulceric and anxiolytic activities.

The term "alkyl group" used throughout the specification relates to straight or branched chained saturated aliphatic hydrocarbon groups having the given number of carbon atom(s), e.g. methyl, ethyl, propyl, isopropyl, n--butyl, tert-butyl etc. The term "alkenyl group" relates to straight or branched chained alkenyl groups containing the given number of carbon atms, e.g. vinyl, allyl, 2-methyl-allyl, 1-propenyl, 1-butenyl, 2-butenyl, 2-hexenyl etc. The term "alkoxy group" relates to alkyl ether groups comprising 1 to 4 carbon atom(s), e.g. methoxy, ethoxy, tert-butoxy etc. The term "halogen atom" encompasses all the four halogen atoms (fluorine, chlorine, bromine and iodine). As "4 to 7 membered ring" aromatic or partially or completely saturated heterocyclic rings are mentioned, which contain as heteroatom a nitrogen and optionally an oxygen, sulfur or further nitrogen atom (e.g. piperidyl, morpholinyl, piperazinyl, furyl, imidazolyl, pyridinyl, pyrazolyl, imidazolyl etc.).

In the preferred representatives of the compounds of general formula (I) $R^1$ and $R^2$ are independently hydrogen or halogen, $R^3$ represents hydrogen or hydroxy, $R^4$ and $R^5$ are independently $C_{1-4}$ alkyl or together form a piperidinyl or pyrrolidinyl group and A and R are as stated above.

Particularly preferred representatives of the compounds of general formula (I) are the following derivatives:

1-phenyl-5-methyl-3-(E)-[2-(dimethylamino)-ethoxyimino]-1-(E)-hexene, 1-(4-chlorophenyl)-6-methyl-3-(E)-[3-(N-piperidinyl)-propoxyimino]-1-(E)-hexene, 1-(4-chlorophenyl)-3-(E)-[2-(N-piperidinyl)-ethoxyimino]-1-(E)-nonene, (R,S)-1-(4-chlorophenyl)-6-methyl-3-(E)-[2-hydroxy-3-(1-piperidinyl)-propoxyimino]-1-(E)-heptene, 1-(4-fluorophenyl)-6-methyl-3-(E)-[3-(N-piperidinyl)-propoxyimino-1-(E)-heptene, 1-(4-chlorophenyl)-6-methyl-3-(Z)-[2-(2-(N-pyrrolidinyl)-ethoxyimino-1-(E)-heptene, 1-(4-chlorophenyl)-6-methyl-3-(E)-[3-(N-pyrrolidinyl)-propoxyimino]-1-(E)-heptene, stereo and optically active isomers and their possible mixtures, acid addition salts and quaternary ammonium derivatives thereof.

Some alkoxyimino derivatives carrying a basic group as substituent are known in the art but their chemical structure and pharmaceutical activity are different from those of the compounds of the present invention.

The fluorene derivative "IPS-339" of formula (a)

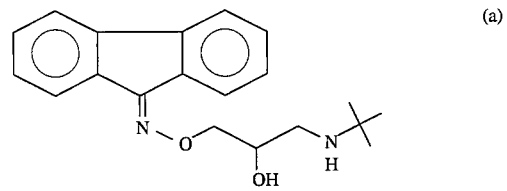

exhibits beta-adrenergic blocking effect.

The methyl cyclopropylketone derivative of formula (b)

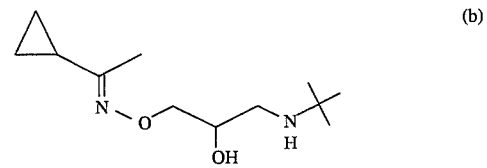

known as Falintolol also exhibits beta-adrenergic blocking activity.

The compound of formula (c)

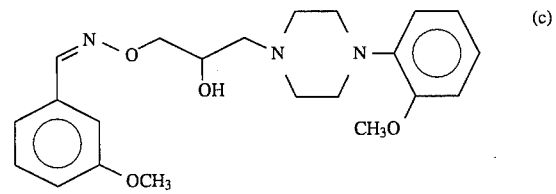

known as Paradoxime possesses blood pressure reducing activity.

Peraclopone (compound of formula d)

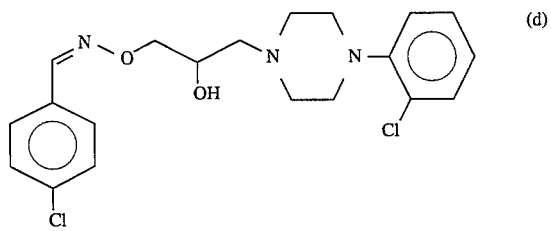

reduces the level of lipids.

The British patent specification No. 1,493,222 describes the compound of formula (e)

(e)

exhibiting local anaesthetic and antiparkinsonic activities.

The Belgian patent specification No. 886,471 describes compounds of formula (VI), $$L{\overset{N}{=}}O{\underset{OH}{\diagdown}}B \quad (VI)$$

wherein L represents benzothiophene group, while B stands for a secondary amine group. The compounds exhibit beta-adrenergic blocking and antiarrhythmic activities.

The published PCT patent application No. 8,402,908 relates to carbostiryl ketoxime derivatives exhibiting not only beta-adrenergic blocking activity but antiglaucomic activity as well.

The Belgian patent specification No. 838,440 describes beta-adrenergic blocking, blood-pressure reducing and cardiovascular compounds of formula (VI), wherein L represents a polycyclic ring (e.g. fluorene, indane, xanthane, tetrahydronaphthalene etc.) or phenyl or naphthyl ketone and B always stands for a secondary amino group.

The U.S. patent specification No. 4,652,586 relates to compounds of formula (VI), wherein L is fluorene and B is a secondary amino group. The compounds reduce the inner pressure of eye and exhibit selective beta-two-adrenergic antagonistic effect.

The European patent specification No. 82,058 describes compounds of formula (f), (f)

wherein $R^1$ represents cyclohexyl, phenyl, benzyl or $C_{1-4}$ alkyl, $R^2$ stands for piperidyl and $R^3$ and $R^4$ each represent straight or branched chained $C_{1-4}$ alkyl, or together with the nitrogen atom to which they are attached form a 4- to 7-membered saturated heterocyclic ring optionally containing a further nitrogen or an oxygen atom and n is an integer from 1 to 4. The compounds exhibit spasmolytic and antihistamine activities.

The European patent specification No. 82,059 relates to oxime ether derivatives of formula (g), (g)

wherein $R^1$ and $R^2$ each represent hydrogen, halogen or $C_{1-4}$ alkyl or together form a methylenedioxy group, $R^3$ is hydrogen or phenyl, which latter carries a $C_{1-4}$ alkyl or halogen substituent, $R^4$ stands for hydrogen and $R^5$ is methyl, or $R^4$ and $R^5$ together represent an alkyl chain containing 3 carbon atms, $R^6$ denotes hydrogen or methyl, $Y^1 Y^2$ each represent $C_{1-4}$ alkyl or together form an alkylene chain containing 4 to 7 carbon atoms, which may contain an oxygen or a nitrogen atom, and n is an integer from 1 to 4. The compounds possess spasmolytic and antihistamine properties and are suitable for the treatment of circulatory disturbances.

The chemical structure of the new basic ethers of general formula (I) is different from that of the prior art compounds and the activity thereof is surprising.

According to another aspect of the present invention there is provided a process for the preparation of basic ethers of general formula (I), stereo and optically active isomers and their possible mixtures, acid addition salts and quaternary ammonium derivatives thereof, which comprises a) reacting a compound of general formula (II), $$R^1\text{-phenyl-}R^2\text{—CH=CH—}\underset{X}{\overset{\|}{C}}\text{—CH}_2\text{—R} \quad (II)$$

wherein X stands for oxygen or sulfur and $R^1$, $R^2$ and R are as stated above, with a hydroxylamine of general formula (III), $$D\text{—CH}_2\text{—}\underset{R^3}{CH}\text{—A—R}^6 \quad (III)$$

wherein D stands for a group of the formula $H_2N\text{—O—}$, $R^6$ represents a group of formula (IV), $$R^7\text{—N}{\diagup}^{R^4}_{\diagdown R^5} \quad (IV)$$

wherein $R^4$ and $R^5$ are as stated above, $R^7$ is a valency bond and $R^3$ is as stated above, or with an acid-addition salt thereof; or b) for the preparation of compounds of general formula (I), wherein $R^3$ represents hydrogen or $C_{1-4}$ alkyl and R, $R^1$, $R^2$, $R^4$ and $R^5$ are as stated above, reacting an oxime of general formula (II), wherein X stands for a group of the formula $=N\text{—OH}$ and $R^1$, $R^2$ and R are as stated above, or an acid-addition salt thereof with a substituted alkane of general formula (III), wherein D stands for halogen, $R^3$ represents hydrogen or $C_{1-4}$ alkyl, A is as stated above and $R^6$ is a group of formula (IV), wherein $R^4$ and $R^5$ are as stated above and $R^7$ represents a valency bond, or with an acid-addition salt thereof in the presence of a basic condensing agent; or c) for the preparation of compounds of general formula (I), wherein $R^3$ represents hydroxy and R, $R^1$, $R^2$, $R^4$ and $R^5$ are as stated above, reacting an oxime of general formula (II), wherein X stands for a group of the formula $=N\text{—OH}$ and $R^1$, $R^2$ and R are as stated above, with a halo compound of general formula (III), wherein D stands for halogen and A, $R^3$ and $R^6$ together represent a group of the formula $\text{—CH}_2\text{—O—}$, in the presence of a basic condensing agent, and reacting the epoxy compound of general formula (V)

(V)

thus obtained, wherein $R^1$, $R^2$ and R are as stated above, with an amine of general formula (IV), wherein $R^7$ represents hydrogen and $R^4$ and $R^5$ are as stated above, and, if possible and desired, converting a compound of general formula (I) thus obtained into a pharmaceutically acceptable acid-addition salt or quaternary ammonium derivative thereof, or liberating the base of general formula (I) from a salt thereof and/or separating the stereo and/or optically active isomers.

According to variant a) of the process of the invention compounds of general formula (II) containing oxygen or sulfur in the place of X are reacted with compounds of general formula (III), wherein D stands for a group of formula $H_2N$—0—, or with the acid addition salts thereof. The reaction is preferably performed in an inert solvent or in a mixture of inert solvents. For this purpose e.g. alcohols, (particularly ethanol), pyridine or triethylamine can be used. The reaction temperature may be varied within wide ranges. The reaction can be performed even at room temperature, but according to our experiments the optimal reaction rate can be achieved at the boiling point of the reaction mixture.

According to variant b) of the process of the invention compounds of general formula (I) containing hydrogen or $C_{1-4}$ alkyl in the place of $R^3$ are prepared. For this purpose compounds of general formula (II), wherein X stands for a =N—OH group are reacted with compounds of general formula (III) containing halogen in the place of D, or with the acid-addition salts of the latter compounds. The reaction is preferably carried out in an inert solvent or in a mixture of inert solvents. Such solvents may be e.g. alcohols (preferably ethanol), benzene or the homologues thereof (toluene, xylene etc.), ethers (e.g. tetrahydrofurane or dibutyl ether), dimethylformamide, diethyl acetamide or the mixtures thereof.

The reaction is carried out in the presence of a basic condensing agent. For this purpose alkali metals (preferably sodium), alkali amides (preferably sodium amide), alkali hydrides (preferably sodium hydride), and alkali hydroxides (preferably sodium hydroxide) can be used.

The temperature of the reaction can vary within wide ranges, from 25° C. to the boiling point of the applied solvent. It is preferable to carry out the reaction between 70° C. and 130° C.

According to variant c) of the process of the present invention compounds of general formula (I), wherein $R^3$ stands for hydroxy, are prepared by reacting compounds of general formula (II) containing a group of formula =N—OH in the place of X with compounds of general formula (III), wherein D is halogen, and by reacting the thus-obtained compound of general formula (V) with an amine of general formula (IV). The reaction of the compounds of general formulae (II) and (III) is carried out in an inert or relatively inert solvent, in the presence of a basic condensing agent. As inert solvent preferably benzene, toluene or dimethylformamide is used. As basic condensing agent an alkali amide or hydride, preferably sodium amide or hydride, or an organic base, preferably pyridine, can be used. Certainly the same result can be achieved when other alkali amides or hydrides are used, but alkali metals can also be used for the same purpose. In this latter case alcohols such as ethanol or propanol are the most preferred solvents. If an alkali hydroxide is applied as basic condensing agent, water is also a suitable solvent. (In this case water is a relatively inert solvent, as it reacts with the epoxy ring after a longer reaction time and at higher temperatures.)

The amination of the epoxy compound of general formula (V) thus obtained can be carried out in an inert medium, such as alcohols (e.g. ethanol) or acetonitrile, but if the reaction is carried out by using amines of higher boiling point, it can be completed even without using any solvent as the amine serves also as a solvent.

The new basic ethers of general formula (I) can be transformed into pharmaceutically acceptable acid-addition salts or quaternary ammonium derivatives by methods known per se. For the preparation of the pharmaceutically acceptable acid-addition salts hydrogen halides, sulfuric acid, phosphoric acid, tartaric acid, succinic acid, acetic acid, fumaric acid, maleic acid, methanesulfonic acid, propionic acid etc. can be used. For the preparation of quaternary ammonium compounds the compounds of general formula (I) are reacted with reactants suitable for quaternarization, e.g. with alkyl halides.

The new basic ethers of general formula (I) may comprise one or two asymmetric carbon atoms depending on the character of the substituents, thus they can be prepared in optically active forms, too. The invention covers all of the racemic and optically active forms of the compounds of general formula (I). If the former compounds of intermediates are prepared in the form of a diastereomeric mixture, they can be separated into the racemic or optically active isomers in a manner known per se, e.g. by fractional distillation, crystallization, chromatography or by forming diastereomeric salts with the aid of optically active acids, such as tartaric acid, dibenzoyltartaric acid or camphorsulfonic acid.

The compounds of general formula (II), wherein X represents oxygen or sulfur, used as starting substances for process variant a) are known and can be prepared e.g. according to the method described in Org. Syn. Coll. 2, 167 (1943). The compounds of general formula (III) containing a group of formula $H_2N$—O— in the place of D used for the same reaction variant can be prepared as described in J. Pharm. Sci. 58, 138 (1969).

The compounds of general formula (II), wherein X represents a group of formula =N—OH, used for process variants b) and c) can be produced according to the method described in Org. Syn. Coll. Vol. 2, 70 (1943).

The compounds of general formula (III) containing a halogen atom in the place of D used for process variants b) and c) can be prepared according to the method specified in Helv. Chim. Acta 41, 1072–1108 (1958) or in Beilstein 17, 1/v 20.

The new basic ethers of general formula (I) proved to be only slightly toxic, at the same time they possess valuable antiulceric and anxiolytic activities.

The biological activity of the new compounds according to the invention is shown by the following tests.

I. Toxicity

The test was carried out according to the method of Litchfield and Wilcoxon [Litchfield, J. T. and Wilcoxon, F. W.: J. Pharmacol. Exp. Ther., 96, 99 (1949)] by using white mice belonging to the CFLP strain and weighing 10 to 22 g, 10 animals per dose. The test compounds were administered orally in a volume of 20 cm$^3$/kg. After treatment the animals were observed for a period of 14 days. The results are summarized in Table I.

TABLE I

| Acute toxicity on mice | | |
|---|---|---|
| Compound | $LD_{50}$ mg/kg | |
| (Example No.) | i.p. | p.o. |
| 17 | 100–300 | >1000 |
| 9 | 160 | >1000 |
| 3 | 100–300 | 500–1000 |
| 35 | 30–100 | >1000 |
| 36 | 30–100 | >1000 |
| 37 | 100–300 | >1000 |
| 38 | 100–300 | 500–1000 |

TABLE I-continued

Acute toxicity on mice

| Compound | LD$_{50}$ mg/kg | |
|---|---|---|
| (Example No.) | i.p. | p.o. |
| 40 | 100–300 | 1000 |
| 41 | 30–100 | >1000 |
| 42 | 100–300 | >1000 |

II. Antiulceric activity
Test methods:

1. H$^+$/K$^+$-ATP-ase inhibition on pig's stomach

The test was carried out according to the method of Rabon and Sachs [E. C. Rabon et al.: Preparation of gastric H$^+$K$^+$-ATP-ase, Methods in Enzymology, 157, 649–651 (1988)]. The activity of the prepared enzyme was measured both in the presence as in the absence of K$^+$ ions. The difference in the libaration of phosphorus representing the activity of the enzyme was measured.

2. The gastric-acid-secretion test was carried out on rats according to the method of Shay et al. [Shay, H., Komarov, S. A., Fels, S. S., Meranze, D., Gruenstein, M., Siplet, H.: Gastroenterology 5, 43–61 (1945)]. The liberated gastric-acid content was determined by titration 4 hours after the ligature of the duodenum.

3. The cytoprotective effect was determined according to the method of Robert [Robert, A.: Cytoprotection by prostaglandins. Gastroenterology 77, 761–767 (1979)]. Rats weighing 200 to 250 g were used as test animals. 1 cm$^3$ of abs. ethanol was introduced to the stomach to produce an erosion of the stomach wall. The length and frequency of the lesions (erosion index and frequency) were measured and the percentage inhibition of lesion formation compared with vehicle-treated animals was calculated.

4. Measurement of $^{14}$C-aminopyrine accumulation by parietal cells

Gastric mucosal cells were prepared from rat stomach. Wistar rats (130–160 g) were killed by decapitation, the stomachs were rapidly excised and their contents were washed out with saline. The stomachs were then everted and filled with 2.5 mg/ml of pronase containing buffer. These sacs were incubated for 60 minutes at 37° C. in carbogen gassed medium. This incubation was followed by gentle stirring at room temperature for 45 minutes by a magnetic stirrer in order to disperse the cells from the mucosa of the everted stomachs digested only from the serosal side. The viability of the cells was determined by trypan-blue exclusion test. The percentage of the parietal cells was determined on the basis of their morphological characteristics.

Acid production of the cells prepared in this way could be induced by cyclic AMP, histamine (in the presence of 3-isobutyl-1-methylxanthine) or carbachol. The acid production was assessed by measuring the accumulation of $^{14}$C-aminopyrine. The undissociated weak base can penetrate into the acid-containing compartments of the cells. In the acidic compartment the aminopyrine dissociates and for the dissociated form the membrane is impermeable. Thus, the distribution of $^{14}$C-aminopyrine between the extracellular and intracellular spaces is an indirect quantitative index for the cellular acid production [W. Schepp, J. Schmidtler, C. Tatge, V. Schusdziarra and M. Classen: Am. J. Physiol. 259 (Gastrointest. Liver Physiol. 22) G646–G654, 1990].

Results

1. The compounds according to the invention are potent inhibitors of the so-called proton pump (H$^+$/K$^+$-ATP-ase) in concentrations about 30 µM or in even lower concentrations. On this basis it can be expected that the compounds will be useful in the treatment of gastric ulcer.

TABLE II

Inhibition of H$^+$/K$^+$-ATP-ase on partially purified pig's microsome specimen

| Compound No. of Example | IC$_{50}$ (µM) |
|---|---|
| 17 | >30 |
| 9 | 12 |
| 3 | 10 |
| 35 | 13 |
| 37 | 21 |
| 38 | 17 |
| 40 | 10 |
| 42 | 7 |
| 41 | 9 |

According to our examinations the compounds according to the invention inhibit the aminopyrine accumulation by rat's parietal cell occurring during the stimulation of gastric-acid secretion. The ED$_{50}$ of the compound according to Example 9 is 0.05 µM.

2. The cytoprotective effect of the compounds is significant, and according to the literature [D. E. Wilson: Therapeutic aspects of prostaglandins in the treatment of peptic ulcer disease. Dig. Dis. Sci. 31, 42–46S (1986)] this is a favourable characteristic considering the potential therapeutic utility.

TABLE III

Gastric-acid-secretion inhibiting and cytoprotective effects

| Compound (No. of Example) | Acid-secretion inhibition, ED$_{50}$ mg/kg, p.o. | Ethanol erosion ED$_{50}$, p.o. | Ratio of acid-secretion inhibition and erosion inhibition |
|---|---|---|---|
| 17 | 166 | 2.7 | 61.4 |
| 9 | 107 | 5.9 | 18.1 |
| 3 | 50–150 | 2.5 | >20 |
| 37 | 30–100 | 3–10 | >10 |
| 38 | 37.7 | 1.3 | 29.0 |
| 40 | <100 | 0.9 | <100 |
| 41 | <100 | 2.0 | <50 |
| Omeprazole | 3.9 | 4.5 | 0.9 |
| Cimetidine | 59.1 | 100–200 | 0.3–0.6 |
| Pirenzepine | 7.9 | 18.6 | 0.4 |
| Sucralfate | — | 69.0 | — |

From the above test results it can be established that the compounds according to the invention are only slightly toxic, at the same time they inhibit the gastric-acid-secretion at doses 3 to 300 times lower than the toxic dose (LD$_{50}$). From the low ED$_{50}$ values obtained in the ethanol erosion test it can be seen that the cytoprotective effect of the test compounds is highly superior to their gastric-acid-secretion inhibiting activity. Our compounds are somewhat less potent inhibitors of the gastric-acid secretion than omeprazole or pirenzepine, but considering the inhibition of the erosion of the stomach wall produced by ethanol they are superior to both reference substances. From this fact it appears that the mechanism of the effect of the new compounds is different from that of the known substances exerting antiulceric activity. The difference demonstrated by the gastric-acid-secretion inhibition/erosion inhibition ratios is very favourable, especially in the treatment of human diseases wherein the injury of the stomach wall occurs simultaneously with a decreased acid production (e.g. gastric disorders caused by alcoholism).

III. Anxiolytic, sedative activity

The compounds according to the invention exert an anxiolytic effect and at the same time they are devoid of any sedative, spontaneous motor activity decreasing side-effect. Certain compounds, when applied in high doses, exhibit a slight antipsychotic effect, too.

1. Anxiolytic effect 1.1. Vogel test (drinking conflict test)

The anxiolytic effect was tested by using the method of Vogel et al. Male Wistar rats of 160 to 180 g body weight were kept free of food and drinking water for 24 and 48 hours, respectively. Test and carrier substances were administered intraperitoneally half an hour before testing. Animals within the experimental chamber were provided with drinking water through an inserted tube. After the animals' each twenty lapping for water the device emitted a 2 mA intensity electric shock through the drinking tube. During 5 minutes the shocks tolerated by the animals in order to quench their thirst were counted. The effect of treatment was expressed as the % increase of the tolerated shocks. The minimum effective dose (MED) was determined for each test compound [Volge, J. R., Beer, B., Clody, D. E.: Psychopharmacologia (Berl.) 21, 1 (1971)]. The data thus obtained are summarized in Table IV.

TABLE IV

| Compound (No. of Example) | MED (mg/kg) |
| --- | --- |
| 21 | 0.03 |
| 19 | 10.0 |
| 18 | 1.0 |
| 17 | 30.0 |
| 15 | 3.0 |
| 14 | 10.0 |
| 13 | >30.0 |
| 10 | 0.1 |
| 5 | >30.0 |
| 7 | 3.0 |
| 1 | 30.0 |
| 9 | >30.0 |
| Meprobamate | 25 |

During the above-specified test several compounds falling under the scope of general formula (I) proved to be more active than the reference compound or showed an activity in the same order of magnitude as Meprobamate.

The compounds of Examples 21 and 10, the most active members in the structural group, were examined in detail in other anxiolytic models, too.

1.2. Elevated plus maze test on rat

The test was carried out with the aid of a wooden plus-shaped maze elevated to a height of 50 cm. Two arms—opposite to one another—were enclosed up to a height of 40 cm along their longer sides and at the end. The other two arms were without walls (open arms). The central 15×15 cm part was open. Male rats belonging to the Sprague Dawley strain and weighing 220 to 260 g were used as test animals. After pretreatment lasting 60 minutes the animals were placed into the central part of the maze. During the 5 minutes observation period the following parameters were recorded:

time spent on the open arms time spent on the closed arms number of open arm entries number of closed arm entries The drug effect was expressed as percent increase of the time spent on the open arms and number of open arm entries. The minimum effective dose which caused a significant increase of the time spent on the open arms was calculated for every substance [Pelow, S., Chopin, P., File, S. E., Briley, M.: J. Neurosci. Methods 14, 149–167 (1985)].

The data are shown in Table V.

TABLE V

| Compound (No. of Example) | MED (mg/kg) p.o. |
| --- | --- |
| 21 | 1.0 |
| 10 | 10.0 |
| Meprobamate | >10.0 |

In order to establish whether the anxiolytic activity is accompanied by a sedative side-effect, the influence of the compounds on the spontaneous motor activity was also investigated.

2. Sedative effect 2.1. Effect on the spontaneous motor activity

The test was carried out according to the method of Borsy et al. Groups consisting of 3 mice each were treated orally with different doses of the compounds to be tested. Then the test animals were placed into a 10-channel Dews system equipment. In this equipment the number of interruptions of infrared beam within 30 minutes was counted. From these data 50% inhibiting doses ($IC_{50}$) were determined with the aid of a line of regression [Borsy, J., Csányi, E., Lázár, I.: Arch. Int. Pharmacodyn. 124, 1 (1960)]. The data are shown in Table VI.

TABLE VI

| Compound (No. of Example) | $ID_{50}$ (mg/kg) | |
| --- | --- | --- |
| 21 | >100 | |
| 19 | >100 | |
| 18 | 100 | mg/kg, inhibition of 54% |
| 17 | >100 | |
| 15 | >100 | |
| 14 | >100 | |
| 13 | >100 | |
| 10 | >100 | |
| 5 | >100 | |
| 7 | >100 | |
| 1 | >100 | |
| 9 | >100 | |
| Chlorodiazepoxide | 56 | |
| Diazepam | 23 | |

From the data of the above Table it can be seen that the compounds according to the invention do not possess a sedative, spontaneous motor activity affecting effect in the anxiolytic dose interval.

3. Antipsychotic effect

Conditioned avoidance response inhibition

The antipsychotic (neuroleptic) effect was measured by the inhibition of the learned conditioned avoidance reflex. The male Wistar rats, used for the study, were of 120–150 g body weight at the commencement of learning. A shuttle box was used as experimental device; it consists of two parts, 24×24.5×23 cm each, separated by a wall with a 6×9 cm gate. In response to a sutiable warning stimulus, in order to avoid the punishing (unconditioned) stimulus, animals within the box passed through the gate from one part to the other. The warning, i.e. conditioned stimulus (CS), a white light (1 Hz) blinking for 15 seconds, was applied at the place of the actual animal existence. The unconditioned stimulus (US), in form of 0.6 mA intensity electric shock, was randomly applied to the paw during the last 5 seconds of the conditioned stimulus. The animal's movement during the CS and US from one part of the box to the other, was defined as avoidance and escape responses, respectively. Both responses ceased the actual stimulus and stopped the trial. The time elapsed until the next trial (intertrial interval, ITI) was 15 seconds. While one experiment was carried out daily, an experiment consisted of 80 trials. Learning efficiency was expressed as percentage of the successful to the total avoidances. Effect of the neuroleptic drugs was examined in animals with stabilized conditioned reflexes and with at least 75% learning efficiency. Dosing was carried out once a week, one hour before the measurement in the shuttle box. To calculate the neuroleptic effect (50% inhibiting dose, $ID_{50}$), results obtained after the treatment were compared to those obtained on the previous day (controls). The obtained data are shown in Table VII.

TABLE VII

Antipsychotic effect

| Compound (No. of Example) | Inhibition of the conditioned reflex (%), 30 mg/kg p.o. |
| --- | --- |
| 21 | 7++ |
| 19 | 19 |
| 18 | 12 |
| 17 | 40++ |
| 15 | 11 |
| 14 | 18++ |
| 13 | 12++ |
| 10 | 13++ |
| 5 | 16++ |
| 7 | 22++ |
| 1 | 10++ |
| 9 | 16++ |
| Thioridazine | $ID_{50}$ = 108.0 |

++ = p < 0.05 (test carried out with two samples)

Only one of the molecules tested (the compound according to Example 17) exhibited a slight conditioned-reflex-inhibiting activity.

Summarizing it can be established that the compounds according to the invention are effective inhibitors of the enzyme responsible for the acid production. They possess a considerable gastric-acid-secretion inhibiting effect in vivo, too. The cytoprotective activity of certain compounds falling under the general formula (I) is outstanding and independent of the proton pump inhibiting effect. The toxicological characteristics of the molecules are favourable, as the $ED_{50}$ values are 100 to 1000 times lower than the acute $LD_{50}$ values. Accordingly, new compounds exerting proton pump inhibiting and cytoprotective activities have been found, which a) are chemically substantially different from the hitherto known molecules having similar effects, so these properties could not be aforeseen on the basis of the chemical structure;

b) possess an enzyme-inhibiting activity being of a μM order of magnitude under the experimental conditions used, c) have an outstanding cytoprotective effect which is independent of the proton pump inhibiting activity.

The molecules showed psychotropic activity in some animal models. The most characteristic feature thereof is the anxiolytic activity without any influence on the spontaneous motor activity. This character is of basic importance considering the human therapy, as it indicates that the compounds according to the invention may be suitable for the treatment of different fear reactions, generalized anxiety disorders or post-traumatic stresses, without decreasing the vigilance and having a sedative potential.

According to a further aspect of the present invention there are provided pharmaceutical compositions comprising as active ingredient at least one compound of general formula (I) or a pharmaceutically acceptable acid-addition salt and/or quaternary ammonium derivative thereof in admixture with suitable inert solid or liquid pharmaceutical carriers.

The pharmaceutical compositions of the present invention can be prepared by methods known per se by admixing the active ingredient with suitable inert solid or liquid carriers or diluents and bringing the mixture to galenic form.

The compounds of general formula (I) can preferably be used in therapy orally in the form of tablets or dragées. The daily dose can vary within wide ranges depending on several factors, e.g. on the activity of the active ingredient, the patient's condition and age, the severity of the disease etc. The oral dose is generally 1 to 300 mg/day. It has to be stressed that the above doses are only of informative character and the administered dose must always be determined by the physician therapeutist.

The compounds of general formula (I) can be used in therapy in the form of solutions or suspensions as well. They can serve as active ingredients for the preparation of pharmaceutical compositions useful in the treatment of disorders caused by hyperacidity (gastric or duodenal ulcer), in the treatment of gastric mucose caused by antiphlogistics (glucocorticoids, salicylic acid derivatives) or for the mitigation of gastric disorders caused by alcoholism.

According to a further aspect of the present invention there is provided the use of the compounds of general formula (I) or pharmaceutically acceptable salts and/or quaternary ammonium derivatives thereof for the preparation of pharmaceutical compositions having particularly ulcus-inhibiting and anxiolytic effects.

According to a still further aspect of the present invention there is provided a method of ulcus-inhibiting and anxiolytic treatment, which comprises administering to the patient an effective amount of a compound of general formula (I) or a pharmaceutically acceptable salt thereof.

The invention is further illustrated by the following Examples of non-limiting character.

EXAMPLE 1

1-Phenyl-3-(E)-[2-(diethylamino)-ethoxyimino]-1-(E)-hexene

1-Phenyl-1-(E)-hexen-3-one-(E)-oxime (18.5 g; 0.1 mole) is transformed into a salt with sodium hydride (4.8 g; 0.1 mole, 50% oily dispersion) in the mixture of dimethylformamide and benzene, and this salt is condensed with 2-chloro-N,N-diethylethylamine (14.9 g; 0.11 mole) at a temperature of 40° to 60° C. The stirring is continued until the oxime cannot be detected in the reaction mixture by thin layer chromatography (Kieselgel $GF_{254}$, eluent: 4:1 mixture of n-hexane and dioxane, UV). The reaction mixture is washed with water, extracted with 0.1N hydrogen chloride solution, precipitated with an aqueous ammonium hydroxide solution, extracted and evaporated.

Yield: 27.2 g (94.5%) of yellow viscous oil. 2-(E)-Butenedioate (1/1) M.p.: 88° to 90° C. Analysis for the formula $C_{22}H_{32}N_2O_5$ (404.5): Calculated: C %=65.32 H %=7.97 N %=6.93 Found: C %=65.53 H %=7.89 N %=6.91. UV: $\lambda_{max}$=291 nm (ε=31203)

EXAMPLE 2

1-Phenyl-6-methyl-3-(E)-[2-(diethylamino)-ethoxyimino]-1-(E)-heptene

One proceeds as described in Example 1 except that instead of 1-phenyl-1-(E)-hexem-3-one-(E)-oxime 21.7 g (0.1 mole) of 1-phenyl-6-methyl-1-(E)-hepten-3-one-(E)-oxime are used.

Yield: 27.6 g (87.3%) of yellowish brown oil. 2-(E)-Butenedioate (1/1) M.p.: 105° to 107° C. Analysis for the formula $C_{24}H_{36}N_2O_5$ (432.5): Calculated: C %=66.64 H %=8.39 N %=6.48 Found: C %=66.53 H %=8.32 N %=6.44. UV: $\lambda_{max}$=288 nm ($\epsilon$=33744)

EXAMPLE 3

1-(4-Chlorophenyl)-3-(E)-[2-(N-piperidinyl)-ethoxyimino]-1-(E)-nonene 1-(4-chlorophenyl)-1-(E)-nonen-3-one-(E)-oxime (26.5 g; 0.1 mole) is reacted with 1-(2-chloroethyl)-piperidine (16.2 g; 0.11 mole) in a solution of 100 g of 10% sodium ethylate in ethanol at the boiling point of the reaction mixture. The reaction is continued until the starting oxime cannot be detected any more in the reaction mixture in the way as specified in Example 1. The mixture is then evaporated, the product is precipitated and filtered off.

Yield: 28.7 g (76.5%) of yellow oil. 2-(E)-Butenedioate (1/1) M.p.: 114° C. Analysis for the formula $C_{26}H_{27}ClN_2O_5$ (493.0): Calculated: C %=63.34 H %=7.56 Cl %=7.19 N %=5.68 Found: C %=63.48 H %=7.52 Cl %=7.22 N %=5.73. UV: $\lambda_{max}$=289 nm ($\epsilon$=30576)

EXAMPLE 4

1-(4-Chlorophenyl)-6-methyl-3-(E)-[2-(N-piperidinyl)-ethoxyimino]-1-(E)-heptene

One proceeds as described in Example 3 except that 1-(4-chlorophenyl)-6-methyl-1-(E)-hepten-3-one-(E)-oxime (26.5 g, 0.1 mole) is used as oxime.

Yield: 29.6 g (81.5%) of yellow oil. 2-(E)-Butenedioate (1/1) M.p.: 128°–130° C. Analysis for the formula $C_{25}H_{35}ClN_2O_5$ (479.0): Calculated: C %=62.68 H %=7.68 Cl %=7.40 N %=5.85 Found: C %=62.59 H %=7.73 Cl %=7.40 N %=5.83. UV: $\lambda_{max}$=289 nm ($\epsilon$=30417).

EXAMPLE 5

1-Phenyl-6-methyl-3-(E)-[3-(dimethylamino)-propoxyimino]-1-(E)-heptene

1-Phenyl-6-methyl-1-(E)-hepten-3-one (20.2 g; 0.1 mole) and O-[3-(dimethylamino)-propyl]-hydroxylamine hydrochloride (19.1 g; 0.1 mole) are boiled in a mixture of 200 cm³ of anhydrous ethanol and 75 cm³ of pyridine for 2 hours. The solvent is then removed in vacuo, the residue is rendered alkaline with an aqueous sodium hydroxide solution (pH=10) at a temperature of 5° C., the base is extracted with dichloroethane, and the organic phase is dried and evaporated.

Yield: 29.6 g (97.8%) of yellow oil. 2-(E)-Butenedioate (1/1) M.p.: 108°–109° C. Analysis for the formula $C_{23}H_{34}N_2O_5$ (418.5): Calculated: C %=66.00 H %=8.19 N %=6.70 Found: C %=65.87 H %=8.22 N %=6.83. UV: $\lambda_{max}$=285 nm ($\epsilon$=27646).

EXAMPLE 6

1-Phenyl-3-(E)-[3-(N-piperidinyl)-propoxyimino]-1-(E)-hexene

One proceeds as specified in Example I except that instead of 2-cloro-N,N-diethylethylamine 1-(3-chloroethyl)piperidine (17.8 g; 0.1 mole) is used. Yield: 30.2 g (96.2%) of yellow oil.

2-(E)-Butenedioate (1/1) M.p.: 91°–93° C. Analysis for the formula $C_{24}H_{34}N_2O_5$ (430.5): Calculated: C %=66.95 H %=7.96 N %=6.51 Found: C %=66.94 H %=7.96 N %=6.55. UV: $\lambda_{max}$=289 nm ($\epsilon$=21693).

EXAMPLE 7

1-(4-Chlorophenyl)-3-(E)-[2-(dimethylamino)-ethoxyimino]-1-(E)-pentene

A solution of 1-(4-chlorophenyl)-1-(E)-penten-3-one-(E)-oxime (21.0 g; 0.1 mole) in dioxane is dropped suspension of potassium amide (5.5 g, 0.1 mole) in 100 cm³ of dioxane. When the gas evolution ceases, a benzene solution of 2-chloro-N,N-dimethylethylamine (11.8 g, 0.11 mole) is added to the suspension. The mixture is reacted at a temperature between 60° C. and 80° C. until the starting oxime cannot be detected any more by thin layer chromatography as described in Example 1. The reaction mixture is then washed with water, extracted with 10% aqueous tartaric acid solution, a concentrated aqueous ammonium hydroxide solution is added to it, it is extracted with dichloromethane, dried and evaporated.

Yield: 23.5 g (83.6%) of yellow oil. 2-(E)-Butenedioate (1/1) M.p.: 160°–162° C. Analysis for the formula $C_{19}H_{25}ClN_2O_5$ (396.9): Calculated: C %=57.40 H %=6.35 Cl %=8.93 N %=7.06 Found: C %=57.30 H %=6.38 Cl %=8.95 N %=7.11. UV: $\lambda_{max}$=292 nm ($\epsilon$=34736).

EXAMPLE 8

(R,S)-1-(4-Chlorophenyl)-6-methyl-3-(E)-{3-[bis(1-methylethyl)-amino]-2-hydroxypropoxyimino}-1-(E)-heptene 1-(4-Chlorophenyl)-6-methyl-1-(E)-hepten-3-one-(E)-oxime (25.2 g; 0.1 mole) is converted into a salt with the aid of sodium hydride (4.8 g; 0.1 mole) in a mixture of dimethylformamide and benzene, at a temperature of 25° C. When the gas evolution ceases, 1-chloro-2,3-epoxypropane (10.2 g; 0.11 mole) is added to the suspension and the mixture is reacted at a temperature of 55° C. to 60° C. for 5 hours. Then it is washed with water, and the organic phase is dried and evaporated. To the residual brown oil (26.1 g) 100 cm³ of anhydrous ethanol and 20.2 g (0.2 mole) of N-(1-methylethyl)-1-methylethylamine are added and the mixture is boiled for 5 hours. The solution is evaporated and the product is precipitated as specified in Example 1.

Yield: 28.4 g (69.5%) of brownish yellow oil. 2-(E)-Butenedioate M.p.: 88°–90° C. Analysis for the formula $C_{27}H_{41}ClN_2O_6$ (525.0): Calculated: C %=61.76 H %=7.87 Cl %=6.75 N %=5.34 Found: C %=61.56 H %=7.93 Cl %=6.63 N %=5.42. UV: $\lambda_{max}$=289 nm ($\epsilon$=28387).

EXAMPLE 9

1-(4-Chlorophenyl)-6-methyl-3-(E)-[3-(N-piperidinyl)-propoxyimino]-1-(E)-heptene One proceeds as specified in Example 6 except that 1-(4-chlorophenyl)-6-methyl-1-(E)-hepten-3-one-(E)-oxime (25.1 g; 0.1 mole) is used as starting substance.

Yield: 34.4 g (91.2%) of yellow oil. 2-(E)-Butenedioate (1/1) M.p.: 121°–124° C. Analysis for the formula $C_{26}H_{37}ClN_2O_5$ (493.0): Calculated: C %=63.34 H %=7.57 Cl %=7.19 N %=5.69 Found: C %=63.32 H % = 7.51 Cl %=7.24 N %=5.72. UV: $\lambda_{max}$=290 nm ($\epsilon$=28269).

EXAMPLE 10

1-Phenyl-5-methyl-3-(E)-[2-(N-piperidinyl)-ethoxyimino]-1-(E)-hexene

One proceeds as specified in Example 3 except that 1-phenyl-5-methyl-1-hexen-3-one-(E)-oxime (20.3 g, 0.1 mole) is used as starting substance.

Yield: 22.8 g (72.4%) of yellow oil. 2-(E)-Butenedioate (1/1) M.p.: 140°–143° C. Analysis for the formula $C_{24}H_{34}N_2O_5$ (430.5): Calculated: C %=66.95 H %=7.96 N %=6.51 Found: C %=67.03 H %=7.89 N %=6.46. UV: $\lambda_{max}$=287 nm ($\epsilon$=24627).

EXAMPLE 11

1-Phenyl-3-(E)-[2-(N-morpholinylethoxyimino]-1-(E)-pentene

One proceeds as specified in Example 1 except that 1-phenyl-1-(E)-penten-3-one-(E)-oxime (17.5 g; 0.1 mole) is used as starting oxime and N-(3-chloroethyl)-morpholine (18.0 g; 0.11 mole) is applied instead of 2-chloro-N,N-diethylethylamine.

Yield: 25.0 g (86.8%) of yellow oil. 2-(E)-Butenedioate (1/1) M.p.: 115°–117° C. Analysis for the formula $C_{21}H_{28}N_2O_6$ (404.4): Calculated: C %=62.36 H %=6.98 N %=6.93 Found: C %=62.43 H %=6.87 N %=6.95. UV: $\lambda_{max}$=286 nm ($\epsilon$=27290).

EXAMPLE 12

1-(4-Chlorophenyl)-3-(E)-[2-(N-piperidinyl)-ethoxyimino]-1-(E)-hexene

One proceeds as specified in Example 3 except that 1-(4-chlorophenyl)-1-(E)-hexen-3-one-(E)-oxime (22.4 g; 0.1 mole) is used as starting oxime.

Yield: 28.8 g (86.0%) of yellow oil. 2-(E)-Butenedioate (1/1) M.p.: 161°–163° C. Analysis for the formula $C_{23}H_{31}ClN_2O_5$ (451.0): Calculated: C %=61.25 H %=6.93 Cl %=7.86 N %=6.21 Found: C %=61.33 H %=6.99 Cl %=7.75 N %=6.31. UV: $\lambda_{max}$=289 nm ($\epsilon$=32150).

EXAMPLE 13

1-(4-Chlorophenyl)-6-methyl-3-(E)-[3-(dimethylamino)-propoxyimino]-1-(E)-heptene 1-(4-Chlorophenyl)-6-methyl-1-(E)-hepten-3-one-(E)-oxime (0.1 mole; 25.1 g) is reacted with 3-chloro-N,N-dimethylpropylamine in a mixture of 50% aqueous potassium hydroxide and 10 g of dimethyl sulfoxide at a temperature between 50° C. and 60° C. for 3 hours. The product is extracted and purified by acidic-alkaline precipitation.

Yield: 30.8 g (91.4%) of yellow oil. 2-(E)-Butenedioate (1/1) M.p.: 115°–120° C. Analysis for the formula $C_{23}H_{33}ClN_2O_5$ (453.0): Calculated: C %=60.98 H %=7.31 Cl %=7.83 N %=6.18 Found: C %=61.01 H %=7.28 Cl %=7.86 N %=6.21. UV: $\lambda_{max}$=291 nm ($\epsilon$=31252).

EXAMPLE 14

1-Phenyl-3-(E)-[2-(dimethylamino)-ethoxyimino]-1-(E)-pentene

One proceeds as specified in Example 7 except that 1-phenyl-1-(E)-penten-3-one-(E)-oxime (17.5 g; 0.1 mole) is used as starting oxime.

Yield: 17.0 g (68.9%) of yellow oil. 2-(E)-Butenedioate (1/1) M.p.: 112°–114° C. Analysis for the formula $C_{19}H_{26}N_2O_5$ (362.4): Calculated: C %=62.97 H %=7.23 N %=7.73 Found: C %=63.05 H %=7.12 N %=7.68. UV: $\lambda_{max}$=284 nm ($\epsilon$=26774).

EXAMPLE 15

1-(4-Chlorophenyl)-6-methyl-3-(E)-2'-(dimethylamino)-ethoxyimino]-1-(E)-heptene

One proceeds as specified in Example 4 except that 2-chloro-N,N-dimethylethylamine (11.9 g; 0.11 mole) is used as alkylating agent.

Yield: 23.7 g (73.4%) of yellow oil. 2-(E)-Butenedioate (1/1) M.p.: 149°–151° C. Analysis for the formula $C_{22}H_{31}ClN_2O_5$ (438.9): Calculated: C %=60.20 H %=7.12 Cl %=8.08 N %=6.38 Found: C %=59.94 H %=7.06 Cl %=8.02 N %=6.31. UV: $\lambda_{max}$=289 nm ($\epsilon$=28671).

EXAMPLE 16

1-Phenyl-3-(E)-[3-(dimethylamino)-propoxyimino]-1-(E)-pentene

One proceeds as specified in Example 11 except that 3-chloro-N,N-dimethylpropylamine (13.4 g; 0.11 mole) is used as alkylating agent.

Yield: 20.7 g (79.6%) of yellow oil. 2-(Z)-Butenedioate (1/1) M.p.: 69°–71° C. Analysis for the formula $C_{20}H_{28}N_2O_5$ (376.3): Calculated: C %=63.81 H %=7.50 N %=7.44 Found: C %=63.72 H %=7.53 N %=7.45. UV: $\lambda_{max}$=286 nm ($\epsilon$=27519).

EXAMPLE 17

1-Phenyl-5-methyl-3-(E)-[2-(dimethylamino)-ethoxyimino]-1-(E)-hexene

One proceeds as specified in Example 7 except that 1-phenyl-5-methyl-1-(E)-hexen-3-one-(E)-oxime (20.3 g; 0.1 mole) is used as starting oxime.

Yield: 20.1 g (73.2%) of yellow oil. 2-(E)-Butenedioate (1/1) M.p.: 133°–135° C. Analysis for the formula $C_{21}H_{30}N_2O_5$ (390.5): Calculated: C %=64.59 H %=7.74 N %=7.17 Found: C %=64.18 H %=7.82 N %=7.21. UV: $\lambda_{max}$=286 nm ($\epsilon$=26696).

EXAMPLE 18

(R,S)-1-Phenyl-3-(E)-[3-(dimethylamino)-2-methylpropoxyimino]-1-(E)-pentene

One proceeds as specified in Example 16 except that 3-chloro-2-N,N-trimethylpropylamine (14.9 g; 0.11 mole) is used for the alkylation.

Yield: 23.3 g (84.9%) of yellow oil. 2-(Z)-Butenedioate (1/1) M.p.: 88°–92° C. Analysis for the formula $C_{21}H_{30}N_2O_5$ (390.5): Calculated: C %=64.59 H %=7.74 N %=7.17 Found: C %=64.63 H %=7.80 N %=7.19. UV: $\lambda_{max}$=277 nm ($\epsilon$=28176).

EXAMPLE 19

(R,S)-1-(4-Chlorophenyl)-3-(E)-[3-(dimethylamino)-2-methylpropoxyimino]-1-(E)-pentene One proceeds as specified in Example 7 except that 3-chloro-2-N,N-trimethylpropylamine (14.9 g; 0.11 mole) is used as alkylating agent.

Yield: 23.7 g (76.8%) of yellow viscous oil, 2-(E)-Butenedioate (1/1) M.p.: 122°–124° C. Analysis for the formula $C_{21}H_{29}ClN_2O_5$ (424.9): Calculated: C %=59.36 H %=6.87 Cl %=8.35 N %=6.59 Found: C %=59.17 H %=6.94 Cl %=8.23 N %=6.66. UV: $\lambda_{max}$=291 nm ($\epsilon$=33817).

EXAMPLE 20

1-(3-Methoxyphenyl)-3-(E)-[2-bis(1-methylethyl)-amino-ethoxyimino]-1-(E)-hexene

One proceeds as specified in Example 1 except that 1-(3-methoxyphenyl)-1-(E)-hexen-3-one-(E)-oxime (21.9 g; 0.1 mole) is used as starting oxime and N-(2-chloroethyl)-N-(1-methylethyl)-2-propylamine (18.0 g; 0.11 mole) is applied as alkylating agent.

Yield: 30.4 g (87.8%) of yellow oil. 2-(E)-Butenedioate (1/1) M.p.: 130°–132° C. Analysis for the formula $C_{25}H_{38}N_2O_6$ (462.6): Calculated: C %=64.91 H %=8.28 N %=6.06 Found: C %=64.78 H %=8.25 N %=6.16. UV: $\lambda_{max}$=280 and 322 nm ($\epsilon$=18863 and 16048).

EXAMPLE 21

1-Phenyl-3-(E)-[3-(dimethylamino)-propoxyimino]-1-(E)-hexene

One procds as specified in Example 1 except that 3-chloro-N,N-dimethylpropylamine (13.4 g; 0.1 mole) is used as alkylating agent.

Yield: 26.6 g (96.8%) of yellowish brown oil. 2-(E)-Butenedioate (1/1) M.p.: 103°–106° C. Analysis for the formula $C_{21}H_{30}N_2O_5$ (390.5): Calculated: C %=64.59 H %=7.74 N %=7.18 Found: C %=64.50 H %=7.82 N %=7.16. UV: $\lambda_{max}$=287 nm ($\epsilon$=29527).

EXAMPLE 22

1-(2-Methoxyphenyl)-3-(E)-[2-(dimethylamino)-ethoxyimino]-1-(E)-hexene

One proceeds as specified in Example 1 except that 2-chloro-N,N-dimethylethylamine (11.8 g; 0.1 mole) is used as alkylating agent and 1-(2-methoxyphenyl)-1-(E)-hexen-3-one-(E)-oxime (21.9 g; 0,1 mole) is applied as starting oxime.

Yield: 25.3 g (87.3%) of yellow oil. 2-(E)-Butenedioate (1/1) M.p.: 115°–117° C. Analysis for the formula $C_{21}H_{30}N_2O_6$ (406.4): Calculated: C %=62.06 H %=7.43 N %=6.89 Found: C %=62.13 H %=7.52 N %=6.91. UV: $\lambda_{max}$=280 and 318 nm ($\epsilon$=18014 and 14705).

EXAMPLE 23

1-(4-Methoxyphenyl)-3-(E)-[2-(diethylamino)-ethoxyimino]-1-(E)-pentene

One proceeds as specified in Example 1 except that 1-(4-methoxyphenyl)-1-(E)-penten-3-one-(E)-oxime (20.5 g; 0.1 mole) is used as starting oxime.

Yield: 30.4 g (83.4%) of yellow oil. 2-(E)-Butenedioate (1/1) M.p.: 114°–116° C. Analysis for the formula $C_{22}H_{32}N_2O_6$ (420.5): Calculated: C %=62.83 H %=7.67 N %=6.66 Found: C %=62.65 H %=7.65 N %=6.68. UV: $\lambda_{max}$=308 nm ($\epsilon$=23548).

EXAMPLE 24

1-(2-Methoxyphenyl)-3-(E)-[3-(dimethylamino)-2-methyl-propoxyimino]-1-(E)-pentene One proceeds as specified in Example 18 except that 1-(2-methoxyphenyl)-1-(E)-penten-3-one-(E)-oxime (20.5 g; 0.2 mole) is used as starting oxime.

Yield: 23.6 g (77.4%) of yellow oil. 2-(E)-Butenedioate (1/1) M.p.: 130°–132° C. Analysis for the formula $C_{22}H_{32}N_2O_6$ (420.5): Calculated: C %=62.83 H %=7.67 N %=6.66 Found: C %=62.57 H %=7.58 N %=6.76. UV: $\lambda_{max}$=278 and 314 nm ($\epsilon$=14998 and 12394).

EXAMPLE 25

1-(4-Methoxyphenyl)-3-(E)-[2-(dimethylamino)-ethoxyimino]-1-(Z,E)-pentene

One proceeds as specified in Example 1 except that 1-(4-methoxyphenyl)-1-(E)-penten-3-one-(E)-oxime (20.5 g; 0.1 mole) is used as starting oxime and 2-chloro-N,N-dimethylethylamine (11.89 g; 0.11 mole) is applied as alkylating agent.

Yield: 17.5 g (63.4%) of yellow oil. 2-(E)-Butenedioate (1/1) M.p.: 138°–139° C. Analysis for the formula $C_{20}H_{28}N_2O_6$ (392.4): Calculated: C %=61.21 H %=7.19 N %=7.14 Found: C %=61.33 H %=7.11 N %=7.08. UV: $\lambda_{max}$=297 nm ($\epsilon$=23469). Isomeric ratio. (Z):(E)=4:3.

EXAMPLE 26

1-(4-Chlorophenyl)-3-(E)-[2-(diethylamino)-ethoxyimino]-1-(E)-pentene

One proceeds as specified in Example 7 except that 2-chloro-N,N-diethylethylamine (14.9 g; 0.11 mole) is used as alkylating agent.

Yield: 25.2 g (81.73%) of yellow oil. 2-(E)-Butenedioate (1/1) M.p.: 162°–165° C. Analysis for the formula $C_{21}H_{29}ClN_2O_5$ (424.9): Calculated: C %=59.36 H %=6.88 N %=6.59 Found: C %=58.99 H %=6.83 N %=6.63. UV: $\lambda_{max}$=288 nm ($\epsilon$=34000).

EXAMPLE 27

1-(4-Chlorophenyl)-3-(E)-[2-(diethylamino)-ethoxyimino]-1-(B)-hexene

One proceeds according to Example 1 except that 1-(4-chlorophenyl)-1-(E)-hexen-3-one-(E)-oxime (22.0 g; 0.1 mole) is used as starting oxime.

Yield: 28.0 g (86.8%) of yellow oil. 2-(E)-Butenedioate (1/1) M.p.: 125°–127° C. Analysis for the formula $C_{22}H_{31}ClN_2O_5$ (438.9): Calculated: C %=60.26 H %=7.13 Cl %=8.09 N %=6.39 Found: C %=60.27 H %=7.21 Cl %=8.11 N %=6.43. UV: $\lambda_{max}$=280 nm ($\epsilon$=34589).

EXAMPLE 28

1-(4-Chlorophenyl)-3-(E)-[2-(dimethylamino)-ethoxyimino]-1-hexene

One proceeds as specified in Example 1 except that 1-(4-chlorophenyl)-1-(E)-hexen-3-one-(E)-oxime (22.0 g; 0.1 mole) is used as starting oxime and 2-chloro-N,N-dimethylethylamine (11.8 g; 0.11 mole) is applied as alkylating agent.

Yield: 23.4 g (79.3%) of yellow oil. 2-(E)-Butenedioate (1/1) M.p.: 132°–135° C. Analysis for the formula $C_{20}H_{21}ClN_2O_5$ (410.9): Calculated: C %=58.46 H %=6.62 Cl %=8.63 N %=6.82 Found: C %=58.58 H %=6.67 Cl %=8.55 N %=6.79. UV: $\lambda_{max}$=280 nm ($\epsilon$=31474).

EXAMPLE 29

(R,S)-1-Phenyl-3-(E)-[3-(dimethylamino)-2-methylpropoxyimino]-1-(E)-butene

A mixture of 1-phenyl-1-(E)-buten-3-one-(E)-oxime (16.2 g; 0.1 mole), 4,4 g (0.11 mole) of sodium hydroxide, 200 cm³ of toluene and 20 cm³ of dimethyl sulfoxide is boiled in a flask equipped with a Marcusson trap until the distillation of water ceases. The sodium salt thus obtained is subjected to condensation with 3-chloro-2,N,N-trimethyl-propylamine (16.2 g; 0.12 mole) at 80° C. until th oxime cannot be detected any more in the reaction mixture in the way as specified in Example 1. The product is purified by acidic-alkaline precipitation.

Yield: 22.7 g (86.7%) of yellow oil. 2-(E)-Butenedioate (1/1) M.p.: 115°–117° C. Analysis for the formula $C_{20}H_{29}N_2O_5$: Calculated: C %=63.64 H %=7.68 N %=7.43 Found: C %=63.58 H %=7.51 N %=7.55. UV: $\lambda_{max}$=285 nm ($\epsilon$=32603).

EXAMPLE 30

1-Phenyl-3-(E)-[3-(4-methyl-1-piperazinyl)-propoxyimino]-1-(E)-butene

One proceeds as specified in Example 29 except that instead of 3-chloro-2,N,N-trimethylpropylamine 1-chloropropyl-4-methylpiperazine (21.1 g; 0.12 mole) is used.

Yield: 27.7 g (91.7%) of yellow oil. 2-(E)-Butenedioate (1/2) M.p.: 208°–210° C. Analysis for the formula $C_{26}H_{35}N_3O_9$ (533.6): Calculated: C %=58.53 H %=6.67 N %=7.87 Found: C %=58.61 H %=6.71 N %=7.83. UV: $\lambda_{max}$=285 nm ($\epsilon$=29983).

EXAMPLE 31

1-Phenyl-3-(E)-[3-(dimethylamino)-propoxyimino]-1-(E)-butene

One proceeds as specified in Example 13 except that instead of 1-(4-chlorophenyl)-6-methyl-1-(E)-hepten-3-one-(E)-oxime 16.2 g (0.1 mole) of 1-phenyl-1-(E)-buten-3-one-(E)-oxime are used.

Yield: 23.3 g (94.2%) of yellow oil. 2-(E)-Butenedioate (1/1) M.p.: 117°–119° C. Analysis for the formula $C_{19}H_{27}N_2O_5$ (363.44): Calculated: C %=64.16 H %=7.66 N %=7.86 Found: C %=63.98 H %=7.17 N %=7.78. UV: $\lambda_{max}$=285 nm ($\epsilon$=31855).

EXAMPLE 32

1-Phenyl-6-methyl-3-(E)-[2-bis-1-(methylethyl)-amino-ethoxyimino]-1-(E)-heptene

One proceeds as specified in Example 1 except that instead of 1-phenyl-1-(E)-hexen-3-one-(E)-oxime 1-phenyl-6-methyl-1-(E)-hepten-3-one-(E)-oxime (23.1 g; 0.1 mole) and instead of 2-chloro-N,N-diethylethylamine 18.01 g (0.11 mole) of N-(2-chloroethyl)-N-(1-methylethyl)-2-propylamine is used.

Yield: 31.1 g (90.2%) of yellow viscous oil. 2-(E)-Butenedioate (1/1) M.p.: 104°–106° C. Analysis for the formula $C_{25}H_{40}N_2O_5$ (460.62): Calculated: C %=67.79 H %=8.75 N %=6.08 Found: C %=67.85 H %=8.48 N %=6.19. UV: $\lambda_{max}$=288 nm ($\epsilon$=29969).

EXAMPLE 33

1-Phenyl-6-methyl-3-(E)-[3-(4-methyl-1-piperazinyl)-propoxyimino]-1-(E)-heptene

One proceeds as specified in Example 32 except that instead of N-(2-chloroethyl)-N-(1-methylethyl)-2-propylamine 1-chloropropyl-4-methylpiperazine (21.1 g; 0.12 mole) is used.

Yield: 32.8 g (91.9%) of yellow viscous oil. 2-(E)-Butenedioate (1/2) M.p.: 206°–211° C. Analysis for the formula $C_{30}H_{43}N_3O_9$ (589.70): Calculated: C %=61.10 H %=7.32 N %=7.18 Found: C %=61.28 H %=7.36 N %=7.12. UV: $\lambda_{max}$=287 nm ($\epsilon$=31791).

EXAMPLE 35

1-(Chlorophenyl)-6-methyl-3-(E)-[3-(hexahydro-1-H-azepinyl)-propoxyimino]-1-(E)-heptene One proceeds as specified in Example 1 except that 1-(4-chlorophenyl)-6-methyl-1-(E)-hepten-3-one-(E)-oxime (25.2 g; 0.1 mole) is used as oxime and instead of 2-chloro-N,N-diethylethylamine 19.1 g (0.11 mole) of N-(3-chloropropyl)-hexahydro-1H-azepine are applied.

Yield: 35.1 g (93.0%) of yellow oil. 2-(E)-Butenedioate (1/1) M.p.: 116°–117° C. Analysis for the formula $C_{27}H_{39}ClN_2O_5$ (493.0): Calculated: C %=63.95 H %=7.75 Cl %=5.52 N %=6.99 Found: C %=63.84 H %=7.79 Cl %=5.61 N %=7.00. UV: $\lambda_{max}$=290 nm ($\epsilon$=29866).

EXAMPLE 36

(R,S)-1-(4-Chlorophenyl)-6-methyl-3-(E)-[3-(cyclohexylamino)-2-hydroxypropoxyimino]-1-(E)-heptene One proceeds as specified in Example 8 except that after the etherification the epoxy group is reacted with cyclohexylamine instead of N-(1-methylethyl)-1-methylethylamine.

Yield: 34.7 g (85.2%) of white crystals. M.p.: 99° C. 2-(E)-Butenedioate (2/1) M.p.: 155° C. Analysis for the formula $C_{25}H_{37}ClN_2O_4$ (465.0): Calculated: C %=64.57 M %=8.02 Cl %=6.03 N %=7.63 Found: C %=64.48 H %=8.04 Cl %=6.12 N %=7.61. UV: $\lambda_{max}$=290 nm ($\epsilon$=31782).

EXAMPLE 37

(R,S)-1-(4-Chlorophenyl)-6-methyl-3-(E)-[2-hydroxy-3-(1-piperidinyl)-propoxyimino]-1-(E)-heptene One proceeds as specified in Example 8 except that the epoxy group is reacted with piperidine.

Yield: 27.2 g (69.4%) of yellow viscous oil. 2-(E)-Butenedioate (1/1) M.p.: 101° to 103° C. Analysis for the formula $C_{26}H_{37}ClN_2O_6$ (509.0): Calculated: C %=61.34 H %=7.32 Cl %=5.50 N %=6.96 Found: C %=61.25 H %=7.28 Cl %=5.44 N %=6.89. UV: $\lambda_{max}$=291 nm ($\epsilon$=30739).

EXAMPLE 38

1-(4-Fluorophenyl)-6-methyl-3-(E)-[3-(N-piperidinyl)-propoxyimino]-1-(E)-heptene One proceeds as specified in Example 1 except that 23.5 g (0.1 mole) of 1-(4-fluorophenyl)-6-methyl-1-(E)-hepten-3-one-(E)-oxime are used as oxime and 1-(3-chloropropyl)-piperidine (17.5 g; 0.11 mole) is applied as alkylating agent.

Yield: 29.4 g (81.4%) of viscous yellow oil. 2-(E)-Butenedioate (1/1) M.p.: 127° to 128° C. Analysis for the formula $C_{26}H_{37}FN_2O_5$ (476.6): Calculated: C %=65.38 H %=7.81 N %=5.87 F %=3.98 Found: C %=65.44 H %=7.80 N %=5.93 F %=3.89. UV: $\lambda_{max}$=283 nm ($\epsilon$=27747).

EXAMPLE 39

1-(4-Chlorophenyl)-6-methyl-3-(E)-[3-(N-morpholinyl)-propoxyimino]-1-(E)-heptene One proceeds as specified in Example 1 except that 25.2 g (0.1 mole) of 1-(4-chlorophenyl)-6-methyl-1-(E)-hepten-3-one-(E)-oxime are used as oxime and 1-(3-chloropropyl)-morpholine (18.0 g; 0.11 mole) is applied for the alkylation.

Yield: 33.5 g (88.3%) of yellow viscous oil. 2-(E)-Butenedioate (1/1) M.p.: 130° to 135° C. Analysis for the formula $C_{25}H_{35}ClN_2O_6$ (495.0): Calculated: C %=60.65 H %=7.13 N %=5.66 Cl %=7.16 Found: C %=60.48 H %=7.11 N %=5.70 Cl %=7.05. UV: $\lambda_{max}$=290 nm ($\epsilon$=28054).

EXAMPLE 40

1-(4-Chlorophenyl)-6-methyl-3-(Z)-[2-(2-N-methylpyrrolidinyl)-ethoxyimino]-1-(E)-heptene One proceeds as specified in Example 39 except that 2-(2-chloroethyl)-N-methylpyrrolidine (16.2 g; 0.11 mole) is used for the alkylation.

Yield: 13.2 g (36.5%) of yellow oil. 2-(Z)-Butenedioate M.p.: 142° to 145° C. Analysis for the formula $C_{25}H_{35}ClN_2O_5$ (479.0): Calculated: C %=62.68 H %=7.37 N %=5.85 Cl %=7.40 Found: C %=62.74 H %=7.49 N %=5.78 Cl %=7.42. UV: $\lambda_{max}$=290 nm ($\epsilon$=32050).

EXAMPLE 41

1-(4-Chlorophenyl)-6-methyl-3-(E)-[3-(N-pyrrolidinyl)-propoxyimino]-1-(E)-heptene One proceeds as specified in Example 39 except that 1-(3-chloropropyl)-pyrrolidine (16.0 g; 0.11 mole) is used for the alkylation.

Yield: 29.2 g (80.5%) of yellow viscous oil. 2-(E)-Butenedioate (1/1) M.p.: 115° to 118° C. Analysis for the formula $C_{25}H_{35}ClN_2O_5$ (479.0): Calculated: C %=62.68 H %=7.37 N %=5.85 Cl %=7.40 Found: C %=62.77 H %=7.43 N %=5.82 Cl %=7.38. UV: $\lambda_{max}$=290 nm ($\epsilon$=31034).

EXAMPLE 42

1-(4-Bromophenyl)-6-methyl-3-(E)-[(3-N-piperidinyl)-propoxyimino]-1-(E)-heptene

One proceeds as specified in Example 6 except that 1-(4-bromophenyl)-6-methyl-1-(E)-hepten-3-one-(E)-oxime (28.6 g; 0.1 mole) is used as oxime.

Yield: 39.3 g (93.2%) of yellow oil. 2-(E)-Butenedioate (1/1) M.p.: 122° to 124° C. Analysis for the formula $C_{26}H_{37}BrN_2O_5$ (537.5): Calculated: C %=58.09 H %=6.94 N %=5.21 Br %=14.87 Found: C %=57.75 H %=7.00 N %=5.17 Br %=14.62. UV: $\lambda_{max}$=282 nm ($\epsilon$=29780).

EXAMPLE 44

1-(3,4-Dichlorophenyl)-6-methyl-3-(E)-[(3 -N-piperidinyl-propyl)-oxyimino]-1-(E)-heptene One proceeds according to Example 38 except that 1-(3,4-dichlorophenyl)-1-(E)-hepten-3-one-(E)-oxime (28.5 g, 0.1 mole) is used as oxime.

Yield: 32.2 g (78.2%) of viscous oil. 2-(E)-Butenedioate (1/1) M.p.: 138° to 139° C. Analysis for the formula $C_{26}H_{36}Cl_2N_2O_5$ (527.49): Calculated: C %=59.30 H %=6.90 Cl %=13.44 N %=5.37 Found: C %=59.30 H %=6.90 Cl %=13.46 N %=5.37. UV: $\lambda_{max}$=300.7 nm ($\epsilon_1$: 32727).

EXAMPLE 45

1-(3,4-Methylenedioxyphenyl)-6-methyl-3-(E)-[(3-N-piperidinyl)-propyloxyimino)-1-(E)-heptene One proceeds as specified in Example 38 except that 1-(3,4-methylenedioxyphenyl)-6-methyl- 1-(E)-hepten-3-one-(E)-oxime (26.0 g, 0.1 mole) is used as oxime.

Yield: 33.7 g (87.2%) of viscous oil. 2-(E)-Butenedioate (1/1) M.p.: 139° to 141.5° C. Analysis for the formula $C_{27}H_{38}N_2O_7$ (502.61): Calculated: C %=64.45 H %=7.86 N %=5.66 Found: C %=64.45 H %=7.83 N %=5.69. UV: $\lambda_{max1}$=329 nm ($\epsilon_1$: 21760). $\lambda_{max2}$=300 nm ($\epsilon_2$: 20226).

EXAMPLE 46

1-(4-Chlorophenyl)-6-methyl-3-(E)-(2-diethylaminoethoxyimino)-1-(E)-heptene

One proceeds as specified in Example 4 except that the alkylation is carried out with 2-chloro-N,N-diethyl-ethyl amine (14.9 g, 0.11 mole).

Yield: 27.7 g (78.9%) of yellow viscous oil. 2-(E)-Butenedioate (1/1) M.p.: 112° to 113° C. Analysis for the formula $C_{24}H_{35}ClN_2O_5$ (466.98): Calculated: C %=61.72 H %=7.55 Cl %=7.59 N %=6.01 Found: C %=61.52 H %=7.63 Cl %=7.51 N %=6.02. UV: $\lambda_{max1}$=289 nm ($\epsilon_1$: 31905).

EXAMPLE 47

(R,S)-1-(4-Chlorophenyl)-6-methyl-3-(E)-[(3-N-pyrrolidinyl-2-hydroxy)-propoxyimino]-1 -(E)-heptene One proceeds as specified in Example 8 except that instead of N-(1-methylethyl)-1-methylethyl amine pyrrolidine (14.2 g, 0.2 mole) is used for the opening of the oxirane ring.

Yield: 20.2 g (62.8%) of yellow viscous oil. 2-(E)-Butenedioate (2/1) M.p.: 132° to 133° C. Analysis for the formula $C_{23}H_{33}ClN_2O_4$ (436.98): Calculated: C %=63.21 H %=7.61 Cl %=8.11 N %=6.41 Found: C %=63.26 H %=7.52 Cl %=8.02 N %=6.51. UV: $\lambda_{max1}$=290 nm ($\epsilon_1$: 31091).

EXAMPLE 48

(R,S)-1-(4-Chlorophenyl)-6-methyl-3-(E)-[(3-dimethylamino-2-hydroxy)-propoxyimino]-1-(E)-heptene One proceeds as specified in Example 8 except that dimethylamine (13.5 g, 0.3 mole) is used for the opening of the oxirane ring.

Yield: 29.1 g (82.4%) of yellow oil. 2-(E)-Butenedioate (1/1) M.p.: 116° to 117° C. Analysis for the formula $C_{23}H_{33}ClN_2O_6$ (468.98): Calculated: C %=58.90 H %=7.09 Cl %=7.56 N %=5.97 Found: C %=58.97 H %=7.12 Cl %=7.53 N %=5.82. UV: $\lambda_{max1}$=292 nm ($\epsilon_1$: 32755).

EXAMPLE 49

(R,S)-1-(4-Methoxyphenyl)-6-methyl-3-(E)-[(3-N-piperidinyl-2-hydroxy)-propoximino]-1 -(E)-heptene One proceeds as specified in Example 8 except that 1-(4-methoxyphenyl)-6-methyl-1-(E)-hepten-3 -one-(E)-oxime (24.7 g, 0.1 mole) is used as oxime and piperidine (17.0 g, 0.2 mole) is applied for the opening of the oxirane ring.

Yield: 34.8 g (89.6%) of yellow oil. 2-(E)-Butenedioate (1/1) M.p.: 129° to 131° C. Analysis for the formula $C_{27}H_{40}N_2O_7$ (504.63): Calculated: C %=64.26 H %=7.99 N %=5.55 Found: C %=64.30 H %=7.95 N %=5.56. UV: $\lambda_{max1}$=296 nm $\epsilon_1$: (28926).

EXAMPLE 50

(R,S)-1-(3,4-Dichlorophenyl)-6-methyl-3-(E)-[(3-N-pyrrolidinyl-2-hydroxy)-propoxyimino]- 1-(E)-heptene One proceeds as specified in Example 47 except that 1-(3,4-dichlorophenyl)-6-methyl-1-(E)-hepten-3 -one-(E)-oxime (28.6 g, 0.1 mole) is used.

Yield: 34.6 g (83.8%) of yellow oil. 2-(E)-Butenedioate (1/1) M.p.: 110° to 111° C. Analysis for the formula $C_{25}H_{34}Cl_2N_2O_6$ (529.47): Calculated: C %=56.72 H %=6.47 Cl %=13.39 N %=5.29 Found: C %=56.50 H %=6.53 Cl %=13.22 N %=5.39. UV: $\lambda_{max1}$=292 nm ($\epsilon_1$: 30029) $\lambda_{max2}$=231 nm ($\epsilon_2$: 17694).

EXAMPLE 51

(R,S)-1-(3,4-Dichlorophenyl)-6-methyl-3-(E)-[(3-cyclopropylamino-2-hydroxy)-propoxyimino]-1-(E)-heptene One proceeds as specified in Example 50 except that instead of pyrrolidine cyclopropyl amine (11.4 g, 0.2 mole) is used for the opening of the oxirane ring.

Yield: 29.1 g (72.8%) of yellow oil. 2-(E)-Butenedioate (1/1) M.p.: 117° to 119° C. Analysis for the formula $C_{24}H_{32}Cl_2N_2O_6$ (515.44): Calculated: C %=55.94 H %=6.26 Cl %=13.76 N %=5.44 Found: C %=55.80 H %=6.18 Cl %=13.49 N %=5.54. UV: $\lambda_{max1}$=292 nm ($\epsilon_1$: 31484) $\lambda_{max2}$=231 nm ($\epsilon_2$: 18192).

EXAMPLE 52

(R,S)-1-(4-Chlorophenyl)-5-methyl-3-(E)-[(3-N-piperidinyl-2-hydroxy)-propoxyimino]-1-(E)-heptene One proceeds as specified in Example 49 except that 1-(4-chlorophenyl)-5-methyl-1-(E)-hexen-3-one-(E)-oxime (23.7 g, 0.1 mole) is used as oxime.

Yield: 29.9 g (84.8%) of yellow oil. Oxalate (1/1) M.p.: 118° to 120° C. Analysis for the formula $C_{23}H_{33}ClN_2O_6$ (468.98): Calculated: C %=58.90 H %=7.09 Cl %=7.57 N %=5.97 Found: C %=58.62 H %=7.01 Cl %=7.42 N %=6.02. UV: $\lambda_{max1}$=224 nm ($\epsilon_1$: 13817) $_{max2}$=292 nm ($\epsilon_2$: 32373).

EXAMPLE 53

(R,S)-1-(3,4-Dichlorophenyl)-6-methyl-3-(E)-[(3-N-piperidinyl-2-hydroxy)-propoxyimino]-1-(E)-heptene One proceeds as specified in Example 50 except that instead of pyrrolidine piperidine (17.0 g, 0.2 mole) is used for the opening of the oxirane ring.

Yield: 34.9 g (81.6%) of yellow oil. 2-(E)-Butenedioate (1/1) M.p.: 134° to 135° C. Analysis for the formula $C_{26}H_{36}Cl_2N_2O_6$ (543.49): Calculated: C %=57.45 H %=6.68 Cl %=13.05 N %=5.16 Found: C %=57.55 H %=6.73 Cl %=12.92 N %=5.25. UV: $\lambda_{max1}$=292 nm ($\epsilon_1$: 31689) $\lambda_{max2}$=231 nm ($\epsilon_2$: 18796).

EXAMPLE 54

(R,S)-1-(4-Methoxyphenyl)-6-methyl-3-(E)-[(3-dimethylamino-2-hydroxy)-propoxyimino]-1-(E)-hexene One proceeds as specified in Example 49 except that instead of piperidine dimethylamine (13.5 g, 0.3 mole) is used for the opening of the oxirane ring.

Yield: 21.93 g (68.0%) of yellow oil. Oxalate (1/1) M.p.: 122° to 124° C. Analysis for the formula $C_{22}H_{34}N_2O_7$ (438.53): Calculated: C %=60.25 H %=7.82 N %=6.38 Found: C %=60.39 H %=7.88 N %=6.47. UV: $\lambda_{max1}$=224 nm ($\epsilon_1$: 13766) $\lambda_{max2}$=292 nm ($\epsilon_2$: 32571).

EXAMPLE 55

(R,S)-1-(4-Chlorophenyl)-5-methyl-3-(E)-[(3-dimethylamino-2-hydroxy)-propoxyimino]-1-(E)-hexene One proceeds as specified in Example 52 except that instead of piperidine dimethylamine (13.5 g, 0.3 mole) is used for the opening of the oxirane ring.

Yield: 26.3 g (83.9%) of yellow oil. Oxalate (1/1) M.p.: 121° to 123° C. Analysis for the formula $C_{20}H_{29}ClN_2O_6$ (428.92): Calculated: C %=56.00 H %=6.82 Cl %=8.27 N %=6.53 Found: C %=56.10 H %=6.79 Cl %=8.13 N %=6.61. UV: $\lambda_{max1}$=226 nm ($\epsilon_1$: 12910) $\lambda_{max2}$=297 nm ($\epsilon_2$: 26141).

EXAMPLE 56

(R,S)-1-(4-Chlorophenyl)-6-methylamino-3-(E)-[(3-N-methyl-2-hydroxy)-propoxyimino]-1-(E)-heptene One proceeds as specified in Example 8 except that methylamine (6.2 g, 0.2 mole) is used for the opening of the oxirane ring.

Yield: 29.3 g (86.7%) of yellow oil. Analysis for the formula $C_{22}H_{31}ClN_2O_6$ (454.96): Calculated: C %=58.08 H %=6.87 Cl %=7.79 N %=6.16 Found: C %=57.80 H %=6.84 Cl %=7.81 N %=6.13. UV: $\lambda_{max1}$=291 nm ($\epsilon_1$: 31299).

EXAMPLE 57

(R,S)-1-(4-Chlorophenyl)-6-methyl-3-(E)-[(3-N-hexyl-2-hydroxy)-propoxyimino]-1-(E)-heptene One proceeds as specified in Example 8 except that 1-aminohexane (20.2 g, 0.2 mole) is used for the opening of the oxirane ring.

Yield: 34.93 g (85.4%) of viscous oil. (E)-2-Butenedioate (2:1) M.p.: 119° to 121° C. Analysis for the formula $C_{25}H_{39}ClN_2O_4$ (467.05): Calculated: C %=64.29 H %=8.42 Cl %=7.59 N %=6.00 Found: C %=64.70 H %=8.50 Cl %=7.32 N %=6.08. UV: $\lambda_{max1}$=291 nm ($\epsilon_1$: 32767).

EXAMPLE 58

Tablet comprising 25 mg of active ingredient

The composition of one tablet is as follows

| | |
|---|---|
| active ingredient | 25.0 mg |
| corn starch | 97.0 mg |
| polyvinyl-pyrrolidone | 175.0 mg |
| magnesium stearate | 3.0 mg |
| | 300.0 mg |

The tablet is prepared as follows:

The active ingredient and the corn starch are admixed, then wetted with 10 to 15% by weight of aqueous polyvinyl-pyrrolidone solution and the mixture is granulated then dried at a temperature of 40° to 50° C. The dry granules are rubbed through a sieve, mixed with magnesium stearate and tablets are prepared from the mixture.

The weight of one tablet is 300.0 mg.

EXAMPLE 59

Tablet comprising 250 mg of active ingredient

The composition of one tablet is as follows:

| | |
|---|---|
| active ingredient | 250.0 mg |
| lactose | 270.0 mg |
| corn starch | 75.0 mg |
| magnesium stearate | 5.0 mg |
| | 600.0 mg |

The active ingredient, lactose and corn starch are wetted and mixed, granulated and dried at a temperature of 40° to 50° C. The dry granules are rubbed through a sieve as described hereinabove, mixed with magnesium stearate, then tablets are formed.

The weight of one tablet is 600.0 mg.

EXAMPLE 60

Dragée comprising 25 mg of active ingredient
The composition of one dragée core is as follows: active ingredient

| | |
|---|---|
| active ingredient | 25.0 mg |
| corn starch | 245.0 mg |
| talc | 18.0 mg |
| gelatin | 8.0 mg |
| magnesium stearate | 4.0 mg |
| | 300.0 mg |

The active ingredient and corn starch are mixed, wetted with 10% by weight aqueous gelatin solution, granules are formed from the wet mixture, then the granules are dried at a temperature of 40° to 50° C. The dry granules are rubbed through a sieve, homogenized with talc and magnesium stearate and dragée cores of 300.0 mg are compressed from the mixture.

EXAMPLE 61

Dragée comprising 50.0 mg of active ingredient

| | |
|---|---|
| active ingredient | 50.0 mg |
| lactose | 97.0 mg |
| polyvinyl-pyrrolidone | 2.0 mg |
| magnesium stearate | 1.0 mg |
| | 150.0 mg |

The granules are prepared as described hereinabove. The weight of the dragée cores is 150 mg.

The dragée cores are coated with a layer containing sugar and talc in a manner known per se. The dragée thus obtained is painted with non-toxic food paint to the desired colour and polished with bee-wax.

EXAMPLE 62

Gelatin capsule comprising 5.0 mg of active ingredient
The composition of one gelatin capsule is as follows:

| | |
|---|---|
| active ingredient | 5.0 mg |
| corn starch | 40.0 mg |
| Aerosil | 3.0 mg |
| magnesium stearate | 2.0 mg |
| | 50.0 mg |

The ingredients are homogenized and filled into gelatin capsules of suitable size.

EXAMPLE 63

Gelatin capsule comprising 25.0 mg of active ingredient
The composition of one gelatin capsule is as follows:

| | |
|---|---|
| active ingredient | 25.0 mg |
| corn starch | 265.0 mg |
| Aerosil | 6.0 mg |
| magnesium stearate | 4.0 mg |
| | 300.0 mg |

The ingredients are homogenized and filled into gelatin capsules of suitable size.

EXAMPLE 64

Gelatin capsule comprising 50.0 mg of active ingredient
The composition of one gelatin capsule is as follows:

| | |
|---|---|
| active ingredient | 50.0 mg |
| lactose | 90.0 mg |
| Aerosil | 6.0 mg |
| magnesium stearate | 4.0 mg |
| | 150.0 mg |

The ingredients are homogenized and filled into gelatin capsules of suitable size.

EXAMPLE 65

Gelatin capsule comprising 250.0 mg of active ingredient
The composition of one gelatin capsule is as follows:

| | |
|---|---|
| active ingredient | 250.0 mg |
| lactose | 148.0 mg |
| magnesium stearate | 2.0 mg |
| | 400.0 mg |

The ingredients are homogenized and filled into gelatin capsules of suitable size.

EXAMPLE 66

Injection comprising 25.0 mg of active ingredient. The composition of one ampoule is as follows:

| | |
|---|---|
| active ingredient | 25.0 mg |
| sodium chloride | 5.0 mg | dissolved in 5 cm$^3$ of twice-distilled water.

The active ingredient and sodium chloride are dissolved in the necessary amount of twice-distilled water suitable for making injections. The solution is filtered, filled into ampoules and sterilized.

EXAMPLE 67

Injection comprising 50.0 mg of active ingredient
The composition of one ampoule is as follows:

| | |
|---|---|
| active ingredient | 50.0 mg |
| sodium chloride | 10.0 mg |

The active ingredient and the sodium chloride are dissolved in the necessary amount of twice-distilled water, then filled into ampoules under sterile conditions.

EXAMPLE 68

Suppository comprising 250 mg of active ingredient
The composition of one suppository is as follows:

| | |
|---|---|
| active ingredient | 250.0 mg |
| fatty acid glyceride | 750.0 mg |

The fatty acid glyceride is melted, the active ingredient is homogenized, then poured into a mould. One suppository weights 1000.0 mg and comprises 250.0 mg of active ingredient.

EXAMPLE 69

Drop comprising 5% by weight of active ingredient

| active ingredient | 50.0 mg |
|---|---|
| sorbitol | 340.0 mg |
| polyethylene glycol | 100.0 mg |
| citric acid | 1.0 mg |
| sodium citrate | 3.0 mg |
| ion-free water | 505.0 mg |
| flavourant | 1.0 mg |
| | 1000.0 mg |

The sorbitol, the active ingredient, citric acid and sodium citrate are dissolved in the aqueous solution of propylene glycol, then after dissolution of the solid materials the flavourant is added. The solution is filtered and filled into flasks supplied with a drop-dispenser.

What we claim is:

1. A basic ether of the formula (I),

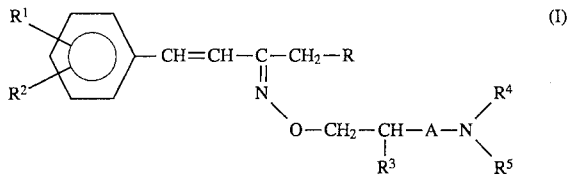

wherein $R^1$ and $R^2$ are independently hydrogen, halogen or $C_{1-4}$ alkoxy, or together they represent a 3,4-methylenedioxy group, R stands for $C_{1-8}$ alkyl, $R^3$ represents hydrogen, $C_{1-4}$ alkyl or hydroxy, A is a valency bond or methylene group, $R^4$ and $R^5$ are independently hydrogen, $C_{1-12}$ alkyl or $C_{1-12}$ alkenyl, or R4 and $R^5$ form together with the adjacent nitrogen atom 1-pyrrolidinyl, 1-piperidinyl, morpholino or 1-piperazinyl groups, its stereo and optically active isomer or racemic mixture, acid-addition or quaternary ammonium salt thereof.

2. A compound of formula (I) as defined in claim 1, wherein $R^1$ and $R^2$ are independently hydrogen or halogen, $R^3$ represents hydrogen or hydroxy, $R^4$ and $R^5$ are independently $C_{1-4}$ alkyl or together they form a piperidinyl or pyrrolidinyl group and A and R are as stated above, its stereo and optically active isomer or racemic mixture, acid-addition or quaternary ammonium salt thereof.

3. The ether according to claim 1, wherein said ether is selected from the group consisting of 1-phenyl-5-methyl-3-(E)-[2-(dimethylamino)-ethoxyimino]-1-(E)-hexene, 1-(4-chlorophenyl)-6-methyl-3-(E)-[3-(N-piperidinyl)-propoxyimino]-1-(E)-heptene, 1-(4-chlorophenyl)-3-(E)-[2-(N-piperidinyl)-ethoxyimino]-1-(E)-nonene, (R,S)-1-(4-chlorophenyl)-6-methyl-3-(E)-[2-hydroxy-3(1-piperidinyl)-propoxyimino]-1-(E)-heptene, 1-(4-fluorophenyl-6-methyl-3-(E)-[3-(N-piperidinyl)-propoxyimino]-1-(E)-heptene, 1-(4-chlorophenyl)-6-methyl-3-(Z)-[2-(2-N-methyl-pyrrolidinyl)-ethoxyimino]-1-(E)-heptene, 1-(4-chlorophenyl)-6-methyl-3-(E)-[3-(N-pyrrolidinyl)-propoxyimino]-1-(E)-heptene, and its stereo and optically active isomer or racemic mixture, acid-addition or quaternary ammonium salt thereof.

4. A pharmaceutical composition comprising as active ingredient at least one compound of general formula (I) as defined in claim 1 or a pharmaceutically acceptable acid-addition salt and/or quaternary ammonium derivative thereof in admixture with suitable inert solid or liquid pharmaceutical carriers.

5. The pharmaceutical composition according to claim 4, wherein said compound is selected from the group consisting of 1-phenyl-5-methyl-3-(E)-[2-(dimethylamino)-ethoxyimino]-1-(E)-hexene, 1-(4-chlorophenyl)-6-methyl-3-(E)-[3-(N-piperidinyl)-propoxyimino]-1-(E)-heptene, 1-(4-chlorophenyl)-3-(E)-[2-(N-piperidinyl)-ethoxyimino]-1-(E)-nonene, (R,S)-1-(4-chlorophenyl)-6-methyl-3-(E)-[2-hydroxy-3(1-piperidinyl)-propoxyimino]-1-(E)-heptene, 1-(4-fluorophenyl)-6-methyl-3-(E)-[3-(N-piperidinyl)-propoxyimino]-1-(E)-heptene, 1-(4-chlorophenyl)-6-methyl-3-(Z)-[2-(2-N-methyl-pyrrolidinyl)-ethoxyimino]-1-(E)-heptene, 1-(4-chlorophenyl)-6-methyl-3-(E)-[3-(N-pyrrolidinyl)-propoxyimino]-1-(E)-heptene, and its stereo and optically active isomer or racemic mixture, acid-addition or quaternary ammonium salt thereof.

6. Method of antiulceric and anxiolytic treatment, which comprises administering to a patient an effective amount of a compound of formula (I) as defined in claim 1 or a pharmaceutically acceptable or quaternary ammonium salt thereof.

7. The method according to claim 6, wherein said effective amount is 1–300 mg/day.

8. The method according to claim 6, wherein said compound is selected from the group consisting of 1-phenyl-5-methyl-3-(E)-[2-(dimethylamino)-ethoxyimino]-1-(E)-hexene, 1-(4-chlorophenyl)-6-methyl-3-(E)-[3-(N-piperidinyl)-propoxyimino]-1-(E)-heptene, 1-(4-chlorophenyl)-3-(E)-[2-(N-piperidinyl)-ethoxyimino]-1-(E)-nonene, (R,S)-1-(4-chlorophenyl)-6-methyl-3-(E)-[2-hydroxy-3(1-piperidinyl)-propoxyimino]-1 -(E)-heptene, 1-(4-fluorophenyl)-6-methyl-3-(E)-[3-(N-piperidinyl)-propoxyimino]-1-(E)-heptene, 1-(4-chlorophenyl)-6-methyl-3-(Z)-[2-(2-N-methyl-pyrrolidinyl)-ethoxyimino]-1-(E)-heptene, 1-(4-chlorophenyl)-6-methyl-3-(E)-[3-(N-pyrrolidinyl)-propoxyimino]-1-(E)-heptene, and its stereo and optically active isomer or racemic mixture, acid-addition or quaternary ammonium salt thereof.

* * * * *